(12) United States Patent
Naidu (10) Patent No.: US 12,239,803 B2
(45) Date of Patent: *Mar. 4, 2025

(54) STABILIZATION DEVICE, SYSTEM, AND METHODS THEREOF FOR INTEGRATED CATHETERS

(71) Applicant: Becton, Dickinson and Company, Franklin Lakes, NJ (US)

(72) Inventor: Jithendra Kumar Sathyanarayana Naidu, Woodlands (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 256 days.

This patent is subject to a terminal disclaimer.

(21) Appl. No.: 17/898,337

(22) Filed: Aug. 29, 2022

(65) Prior Publication Data
US 2022/0409862 A1 Dec. 29, 2022

Related U.S. Application Data

(63) Continuation of application No. 16/825,834, filed on Mar. 20, 2020, now Pat. No. 11,426,557.
(Continued)

(51) Int. Cl.
*A61M 25/02* (2006.01)
(52) U.S. Cl.
CPC ....... *A61M 25/02* (2013.01); *A61M 2025/024* (2013.01); *A61M 2025/0266* (2013.01)
(58) Field of Classification Search
CPC .... A61M 2025/024; A61M 2025/0266; A61M 25/02; A61M 2025/0246; A61M 2025/0253; A61M 2025/028
See application file for complete search history.

(56) References Cited

U.S. PATENT DOCUMENTS 6,663,600 B2   12/2003   Bierman et al.
6,673,046 B2   1/2004    Bierman et al.
(Continued)

FOREIGN PATENT DOCUMENTS

ES     2264219 T3      12/2006
WO     2015134250 A1   9/2015

OTHER PUBLICATIONS

PCT/US2020/024010 filed Mar. 20, 2020 International Search Report and Written Opinion dated Jun. 2, 2020.
(Continued)

*Primary Examiner* — Deanna K Hall
(74) *Attorney, Agent, or Firm* — Rutan & Tucker LLP (57) ABSTRACT

A stabilization device for integrated catheters can include a platform, a pair of catheter fasteners on the platform, and a pair of stabilization wings extending from the platform. The platform can include a skin-facing side and catheter-securing side of the platform. The pair of catheter fasteners can be on the catheter-securing side of the platform. The catheter fasteners can be configured to secure a hub of an integrated catheter having an extension port. The pair of stabilization wings can extend from a transverse axis of the platform. The stabilization wings can be configured to mitigate rotation of the integrated catheter about a longitudinal axis thereof when the integrated catheter is secured by the catheter fasteners on the platform and the stabilization device is adhered to a patient. A method for stabilizing integrated catheters can include securing an integrated catheter and adhering the stabilization device to a patient's skin.

15 Claims, 8 Drawing Sheets

Related U.S. Application Data (60) Provisional application No. 62/822,721, filed on Mar. 22, 2019.

(56) References Cited

U.S. PATENT DOCUMENTS

| | | |
|---|---|---|
| 6,689,104 B2 | 2/2004 | Bierman |
| 6,796,310 B2 | 9/2004 | Bierman |
| 6,827,705 B2 | 12/2004 | Bierman |
| 6,827,707 B2 | 12/2004 | Wright et al. |
| 6,866,652 B2 | 3/2005 | Bierman |
| 6,929,625 B2 | 8/2005 | Bierman |
| 6,948,500 B2 | 9/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 7,014,627 B2 | 3/2006 | Bierman |
| 7,018,362 B2 | 3/2006 | Bierman et al. |
| 7,153,291 B2 | 12/2006 | Bierman |
| 7,204,827 B2 | 4/2007 | Kessler |
| 7,223,256 B2 | 5/2007 | Bierman |
| 7,247,150 B2 | 7/2007 | Bierman |
| 7,354,421 B2 | 4/2008 | Bierman |
| 7,491,190 B2 | 2/2009 | Bierman et al. |
| 7,520,870 B2 | 4/2009 | Bierman |
| 7,563,251 B2 | 7/2009 | Bierman et al. |
| 7,568,484 B2 | 8/2009 | Bierman et al. |
| 7,578,804 B2 | 8/2009 | Bierman |
| 7,591,803 B2 | 9/2009 | Bierman |
| 7,628,154 B2 | 12/2009 | Bierman et al. |
| 7,628,771 B2 | 12/2009 | Kessler |
| 7,635,355 B2 | 12/2009 | Bierman |
| 7,648,492 B2 | 1/2010 | Bierman |
| 7,651,479 B2 | 1/2010 | Bierman |
| 7,666,167 B2 | 2/2010 | Bierman |
| 7,722,571 B2 | 5/2010 | Bierman et al. |
| 7,744,572 B2 | 6/2010 | Bierman |
| 7,762,991 B2 | 7/2010 | Bierman et al. |
| 7,785,295 B2 | 8/2010 | Bierman |
| 7,799,001 B2 | 9/2010 | Bierman |
| 7,806,873 B2 | 10/2010 | Dikeman et al. |
| 7,811,258 B2 | 10/2010 | Bierman |
| 7,837,655 B2 | 11/2010 | Bierman et al. |
| 7,879,013 B2 | 2/2011 | Smith et al. |
| 7,887,515 B2 | 2/2011 | Bierman |
| 7,935,083 B2 | 5/2011 | Bierman et al. |
| 7,935,084 B2 | 5/2011 | Bierman |
| 7,955,307 B2 | 6/2011 | Bierman et al. |
| 7,967,792 B2 | 6/2011 | Bierman |
| 7,972,310 B2 | 7/2011 | Kessler |
| 7,985,206 B2 | 7/2011 | Dikeman et al. |
| 7,988,673 B2 | 8/2011 | Wright et al. |
| 8,016,792 B2 | 9/2011 | Wright et al. |
| 8,016,793 B2 | 9/2011 | Wright et al. |
| 8,025,060 B2 | 9/2011 | Bierman |
| 8,025,643 B2 | 9/2011 | Bierman |
| 8,043,280 B2 | 10/2011 | Bierman |
| 8,052,648 B2 | 11/2011 | Dikeman et al. |
| 8,052,649 B2 | 11/2011 | Wright |
| 8,052,652 B2 | 11/2011 | Bierman et al. |
| 8,057,440 B2 | 11/2011 | Bierman |
| 8,074,651 B2 | 12/2011 | Bierman et al. |
| 8,100,862 B2 | 1/2012 | Bierman |
| 8,105,289 B2 | 1/2012 | Bierman et al. |
| 8,105,290 B2 | 1/2012 | Wright et al. |
| 8,114,054 B2 | 2/2012 | Bierman et al. |
| 8,146,210 B2 | 4/2012 | Nishtala |
| 8,162,898 B1 | 4/2012 | Wright |
| 8,172,807 B2 | 5/2012 | Dikeman et al. |
| 8,177,756 B2 | 5/2012 | Wright |
| 8,197,447 B2 | 6/2012 | Wright |
| 8,211,063 B2 | 7/2012 | Bierman et al. |
| 8,241,253 B2 | 8/2012 | Bracken |
| 8,246,583 B2 | 8/2012 | Bierman |
| 8,251,956 B2 | 8/2012 | Bierman et al. |
| 8,269,059 B2 | 9/2012 | Wright et al. |
| 8,277,420 B2 | 10/2012 | Bierman et al. |
| 8,282,606 B2 | 10/2012 | Bierman |
| 8,298,191 B2 | 10/2012 | Bierman et al. |
| 8,333,736 B2 | 12/2012 | Wright et al. |
| 8,357,124 B2 | 1/2013 | Bierman |
| 8,366,678 B2 | 2/2013 | Bierman et al. |
| 8,394,065 B2 | 3/2013 | Bierman |
| 8,394,067 B2 | 3/2013 | Bracken et al. |
| 8,398,599 B2 | 3/2013 | Bierman |
| 8,465,458 B2 | 6/2013 | Bierman |
| 8,506,531 B2 | 8/2013 | Bierman |
| 8,540,680 B2 | 9/2013 | Burn |
| 8,585,655 B2 | 11/2013 | Bierman |
| 8,608,704 B2 | 12/2013 | Bierman |
| 8,608,705 B2 | 12/2013 | Peters et al. |
| 8,636,698 B2 | 1/2014 | Bierman et al. |
| 8,636,701 B2 | 1/2014 | Henry et al. |
| 8,641,678 B2 | 2/2014 | Bierman |
| 8,657,791 B2 | 2/2014 | Bierman et al. |
| 8,679,066 B2 | 3/2014 | Aviles |
| 8,679,067 B2 | 3/2014 | Wright |
| 8,684,976 B2 | 4/2014 | Bierman et al. |
| 8,708,967 B2 | 4/2014 | Bierman |
| 8,728,039 B2 | 5/2014 | Bierman et al. |
| 8,734,400 B2 | 5/2014 | Ciccone |
| 8,740,852 B2 | 6/2014 | Aviles |
| 8,827,959 B2 | 9/2014 | Wright et al. |
| 8,834,424 B2 | 9/2014 | Parvatiyar et al. |
| 8,834,425 B2 | 9/2014 | Bracken et al. |
| 8,840,589 B2 | 9/2014 | Bierman et al. |
| 8,900,196 B2 | 12/2014 | Andino |
| 8,915,885 B2 | 12/2014 | Smith et al. |
| 9,017,290 B2 | 4/2015 | Peters et al. |
| 9,056,186 B2 | 6/2015 | Wright et al. |
| 9,061,122 B2 | 6/2015 | Bierman et al. |
| 9,067,013 B2 | 6/2015 | Wright et al. |
| 9,138,560 B2 | 9/2015 | Wright et al. |
| 9,415,191 B2 | 8/2016 | Aviles |
| 9,468,740 B2 | 10/2016 | Bierman et al. |
| 9,480,821 B2 | 11/2016 | Ciccone et al. |
| 9,526,871 B2 | 12/2016 | Wright et al. |
| 9,561,348 B2 | 2/2017 | Bierman |
| 9,604,034 B2 | 3/2017 | Andino |
| 9,616,200 B2 | 4/2017 | Smith et al. |
| 9,642,987 B2 | 5/2017 | Bierman et al. |
| 9,694,130 B2 | 7/2017 | Andino et al. |
| 9,700,700 B2 | 7/2017 | Andino et al. |
| 9,731,097 B2 | 8/2017 | Andino et al. |
| 9,962,524 B2 | 5/2018 | Andino |
| 9,974,929 B2 | 5/2018 | Ciccone et al. |
| 9,993,619 B2 | 6/2018 | Bracken et al. |
| 10,245,415 B2 | 4/2019 | Andino et al. |
| 10,322,262 B2 | 6/2019 | Bracken et al. |
| 10,426,928 B2 | 10/2019 | Andino et al. |
| 10,537,714 B2 | 1/2020 | Andino et al. |
| 10,561,815 B2 | 2/2020 | Bierman et al. |
| 10,589,067 B2 | 3/2020 | Ciccone |
| 10,729,887 B2 | 8/2020 | Andino et al. |
| 11,020,565 B2 | 6/2021 | Spitler |
| 11,420,023 B2 | 8/2022 | Andino et al. |
| 11,426,557 B2 * | 8/2022 | Naidu ............... A61M 25/02 |
| 2002/0068904 A1 | 6/2002 | Bierman et al. |
| 2002/0133121 A1 | 9/2002 | Bierman |
| 2002/0165493 A1 | 11/2002 | Bierman |
| 2002/0165494 A1 | 11/2002 | Bierman et al. |
| 2002/0187259 A1 | 12/2002 | Bierman |
| 2002/0188255 A1 | 12/2002 | Bierman et al. |
| 2002/0188257 A1 | 12/2002 | Bierman |
| 2003/0083625 A1 | 5/2003 | Bierman |
| 2003/0089374 A1 | 5/2003 | Bierman |
| 2003/0125668 A1 | 7/2003 | Bierman |
| 2003/0229313 A1 | 12/2003 | Bierman |
| 2004/0034330 A1 | 2/2004 | Bierman et al. |
| 2004/0102736 A1 | 5/2004 | Bierman |
| 2004/0138624 A1 | 7/2004 | Bierman |
| 2004/0167475 A1 | 8/2004 | Wright et al. |
| 2004/0199122 A1 | 10/2004 | Bierman et al. |
| 2004/0204684 A1 | 10/2004 | Bierman |
| 2004/0226565 A1 | 11/2004 | Bierman |

(56) References Cited

U.S. PATENT DOCUMENTS

| | | |
|---|---|---|
| 2005/0010173 A1 | 1/2005 | Bierman et al. |
| 2005/0027258 A1 | 2/2005 | Bierman et al. |
| 2005/0075610 A1 | 4/2005 | Bierman |
| 2005/0131351 A1 | 6/2005 | Bierman |
| 2005/0192539 A1 | 9/2005 | Bierman et al. |
| 2005/0192540 A1 | 9/2005 | Kessler |
| 2005/0263158 A1 | 12/2005 | Bierman |
| 2005/0273058 A1 | 12/2005 | Bierman |
| 2006/0064063 A1 | 3/2006 | Bierman |
| 2006/0089600 A1 | 4/2006 | Bierman et al. |
| 2006/0124133 A1 | 6/2006 | Bierman et al. |
| 2006/0129103 A1 | 6/2006 | Bierman et al. |
| 2006/0135944 A1 | 6/2006 | Bierman |
| 2006/0184127 A1 | 8/2006 | Bierman |
| 2006/0184128 A1 | 8/2006 | Bierman |
| 2006/0184129 A1 | 8/2006 | Bierman |
| 2006/0247577 A1 | 11/2006 | Wright |
| 2006/0264836 A1 | 11/2006 | Bierman |
| 2006/0270994 A1 | 11/2006 | Bierman |
| 2006/0270995 A1 | 11/2006 | Bierman |
| 2006/0276752 A1 | 12/2006 | Bierman et al. |
| 2007/0055205 A1 | 3/2007 | Wright et al. |
| 2007/0066958 A1 | 3/2007 | Wright |
| 2007/0068533 A1 | 3/2007 | Bierman et al. |
| 2007/0088329 A1 | 4/2007 | Bierman |
| 2007/0142784 A1 | 6/2007 | Dikeman et al. |
| 2007/0149930 A1 | 6/2007 | Bierman |
| 2007/0156097 A1 | 7/2007 | Bierman |
| 2007/0167915 A1 | 7/2007 | Bierman |
| 2007/0173766 A1 | 7/2007 | Bierman |
| 2007/0173769 A1 | 7/2007 | Kessler |
| 2007/0219500 A1 | 9/2007 | Wright et al. |
| 2007/0265572 A1 | 11/2007 | Smith et al. |
| 2007/0276332 A1 | 11/2007 | Bierman |
| 2007/0276333 A1 | 11/2007 | Bierman |
| 2007/0276334 A1 | 11/2007 | Bierman et al. |
| 2007/0276335 A1 | 11/2007 | Bierman |
| 2007/0276336 A1 | 11/2007 | Bierman et al. |
| 2007/0282273 A1 | 12/2007 | Bierman |
| 2007/0287963 A1 | 12/2007 | Bierman |
| 2008/0027391 A1 | 1/2008 | Bierman |
| 2008/0027392 A1 | 1/2008 | Bierman |
| 2008/0027393 A1 | 1/2008 | Bierman |
| 2008/0027394 A1 | 1/2008 | Bierman |
| 2008/0039798 A1 | 2/2008 | Bierman |
| 2008/0077118 A1 | 3/2008 | Bierman |
| 2008/0097334 A1 | 4/2008 | Dikeman et al. |
| 2008/0132848 A1 | 6/2008 | Wright et al. |
| 2008/0154208 A1 | 6/2008 | Bierman |
| 2008/0249476 A1 | 10/2008 | Bierman et al. |
| 2009/0036835 A1 | 2/2009 | Bierman |
| 2009/0043260 A1 | 2/2009 | Bierman |
| 2009/0093766 A1 | 4/2009 | Bierman et al. |
| 2009/0093769 A1 | 4/2009 | Wright et al. |
| 2009/0137961 A1 | 5/2009 | Bracken |
| 2009/0137962 A1 | 5/2009 | Bracken et al. |
| 2009/0139061 A1 | 6/2009 | Nishtala |
| 2009/0143740 A1 | 6/2009 | Bierman et al. |
| 2009/0143741 A1 | 6/2009 | Bum |
| 2009/0143742 A1 | 6/2009 | Bracken et al. |
| 2009/0143744 A1 | 6/2009 | Bierman et al. |
| 2009/0145440 A1 | 6/2009 | Bierman et al. |
| 2009/0182283 A1 | 7/2009 | Sloan |
| 2009/0254040 A1 | 10/2009 | Bierman et al. |
| 2009/0259188 A1 | 10/2009 | Bierman et al. |
| 2009/0306603 A1 | 12/2009 | Bierman et al. |
| 2009/0326474 A1 | 12/2009 | Bierman et al. |
| 2010/0022962 A1 | 1/2010 | Bierman et al. |
| 2010/0100051 A1 | 4/2010 | Bierman |
| 2010/0114034 A1 | 5/2010 | Wright et al. |
| 2010/0137807 A1 | 6/2010 | Kessler |
| 2010/0179481 A1 | 7/2010 | Bierman et al. |
| 2010/0179482 A1 | 7/2010 | Wright et al. |
| 2010/0179483 A1 | 7/2010 | Wright et al. |
| 2010/0180900 A1 | 7/2010 | Talsma et al. |
| 2010/0222748 A1 | 9/2010 | Bierman et al. |
| 2010/0298777 A1 | 11/2010 | Nishtala |
| 2010/0298778 A1 | 11/2010 | Bracken et al. |
| 2010/0324491 A1 | 12/2010 | Bierman et al. |
| 2011/0021998 A1 | 1/2011 | Dikeman et al. |
| 2011/0054409 A1 | 3/2011 | Nishtala |
| 2011/0112483 A1 | 5/2011 | Smith et al. |
| 2011/0178467 A1 | 7/2011 | Bierman et al. |
| 2011/0202010 A1 | 8/2011 | Bierman |
| 2011/0213310 A1 | 9/2011 | Bierman |
| 2011/0218498 A1 | 9/2011 | Bierman et al. |
| 2011/0230843 A1 | 9/2011 | Bierman et al. |
| 2011/0240034 A1 | 10/2011 | Ciccone |
| 2011/0245777 A1 | 10/2011 | Andino et al. |
| 2011/0257600 A1 | 10/2011 | Kessler |
| 2011/0264050 A1 | 10/2011 | Henry et al. |
| 2011/0282291 A1 | 11/2011 | Ciccone |
| 2011/0282294 A1 | 11/2011 | Dikeman et al. |
| 2011/0288487 A1 | 11/2011 | Wright et al. |
| 2011/0288489 A1 | 11/2011 | Bierman et al. |
| 2011/0295173 A1 | 12/2011 | Wright et al. |
| 2011/0295210 A1 | 12/2011 | Wright |
| 2011/0313362 A1 | 12/2011 | Bierman |
| 2011/0319830 A1 | 12/2011 | Peters et al. |
| 2012/0029484 A1 | 2/2012 | Gusmao et al. |
| 2012/0041378 A1 | 2/2012 | Bierman |
| 2012/0046649 A1 | 2/2012 | Bierman |
| 2012/0053526 A1 | 3/2012 | Bierman et al. |
| 2012/0059328 A1 | 3/2012 | Dikeman et al. |
| 2012/0059329 A1 | 3/2012 | Bierman |
| 2012/0123343 A1 | 5/2012 | Aviles |
| 2012/0136314 A1 | 5/2012 | Ciccone et al. |
| 2012/0143140 A1 | 6/2012 | Bierman et al. |
| 2012/0150117 A1 | 6/2012 | Andino |
| 2012/0184915 A1 | 7/2012 | Bierman et al. |
| 2012/0197202 A1 | 8/2012 | Wright et al. |
| 2012/0197205 A1 | 8/2012 | Peters |
| 2012/0215173 A1 | 8/2012 | Wright |
| 2012/0220947 A1 | 8/2012 | Dikeman et al. |
| 2012/0232488 A1 | 9/2012 | Aviles |
| 2012/0232490 A1 | 9/2012 | Andino |
| 2012/0265147 A1 | 10/2012 | Andino et al. |
| 2012/0271237 A1 | 10/2012 | Andino |
| 2012/0271239 A1 | 10/2012 | Andino et al. |
| 2012/0271240 A1 | 10/2012 | Andino et al. |
| 2012/0316505 A1 | 12/2012 | Wright |
| 2013/0018322 A1 | 1/2013 | Wright et al. |
| 2013/0053785 A1 | 2/2013 | Parvatiyar et al. |
| 2013/0079723 A1 | 3/2013 | Andino et al. |
| 2013/0138045 A1 | 5/2013 | Bierman |
| 2013/0138080 A1 | 5/2013 | Andino et al. |
| 2013/0150827 A1 | 6/2013 | Bracken et al. |
| 2013/0345639 A1 | 12/2013 | Spittler |
| 2014/0188078 A1 | 7/2014 | Peters et al. |
| 2014/0249478 A1 | 9/2014 | Bierman et al. |
| 2014/0276542 A1 | 9/2014 | Ciccone |
| 2014/0276544 A1 | 9/2014 | Aviles |
| 2014/0343501 A1 | 11/2014 | Bierman et al. |
| 2015/0088076 A1 | 3/2015 | Andino |
| 2015/0112270 A1 | 4/2015 | Smith et al. |
| 2015/0367102 A1 | 12/2015 | Andino et al. |
| 2016/0008577 A1 | 1/2016 | Wright et al. |
| 2017/0043131 A1 | 2/2017 | Ciccone et al. |
| 2017/0216556 A1 | 8/2017 | Bierman et al. |
| 2017/0296788 A1 | 10/2017 | Andino et al. |
| 2017/0296789 A1 | 10/2017 | Andino et al. |
| 2019/0247625 A1 | 8/2019 | Bracken et al. |
| 2020/0030578 A1 | 1/2020 | Andino et al. |
| 2020/0171273 A1 | 6/2020 | Bierman et al. |
| 2020/0215309 A1 | 7/2020 | Ciccone |
| 2020/0297975 A1 | 9/2020 | Naidu |
| 2020/0324085 A1 | 10/2020 | Andino et al. |
| 2021/0283375 A1 | 9/2021 | Spitler |

OTHER PUBLICATIONS uS16/825,834 filed Mar. 20, 2020 Non-Final Office Action dated Nov. 4, 2021.

(56) References Cited

OTHER PUBLICATIONS uS16/825,834 filed Mar. 20, 2020 Notice of Allowance dated Apr. 13, 2022.
EP 207797853 filed Sep. 30, 2021 Extended European Search Report dated Nov. 21, 2022.

* cited by examiner

STABILIZATION DEVICE, SYSTEM, AND METHODS THEREOF FOR INTEGRATED CATHETERS

PRIORITY

This application is a continuation of U.S. patent application Ser. No. 16/825,834, filed Mar. 20, 2020, now U.S. Pat. No. 11,426,557, which claims the benefit of priority to U.S. Provisional Application No. 62/822,721, filed Mar. 22, 2019, each of which is incorporated by reference in its entirety into this application.

BACKGROUND

A peripheral intravenous catheter ("PIVC") often needs to be prematurely removed from a patient before an intended IV therapy is complete. A primary factor contributing to the need to prematurely remove a PIVC is mechanical phlebitis, which results when the PIVC moves and irritates the internal anatomy of the patient. A secondary factor contributing to the need to prematurely remove a PIVC is potential introduction of microorganisms when the PIVC moves while within the patient. Mechanical stabilization of PIVCs has been shown to decrease mechanical phlebitis and increase IV-therapy dwell time. However, existing stabilization devices for such PIVCs are not compatible with integrated PIVCs. Thus, the existing stabilization devices cannot provide the mechanical stabilization needed to reduce mechanical phlebitis and enhance the dwell time needed to complete intended IV therapies with integrated PIVCs. Disclosed herein is a stabilization device and methods thereof for integrated catheters such as integrated PIVCs.

SUMMARY

Disclosed herein is a stabilization device for integrated catheters including, in some embodiments, a platform, a pair of catheter fasteners on the platform, and a pair of stabilization wings extending from the platform. The platform has a skin-facing side and catheter-securing side of the platform. The pair of catheter fasteners is on the catheter-securing side of the platform. The catheter fasteners are configured to secure a hub of an integrated catheter having an extension port. The pair of stabilization wings extend from a transverse axis of the platform. The stabilization wings are configured to mitigate rotation of the integrated catheter about a longitudinal axis thereof when the integrated catheter is secured by the catheter fasteners on the platform and the stabilization device is adhered to a patient.

In some embodiments, the platform is configured with a degree of flexibility enabling the platform to conform to a contour of the patient at a stabilization site thereof.

In some embodiments, the skin-facing side of the platform has an adhesive thereon configured to adhere to skin of the patient.

In some embodiments, the stabilization device further includes a pad of a foam-like material having a skin-facing side and a platform-facing side of the pad. The pad is configured with a degree of compressibility enabling the pad to conform to a contour of the patient at a stabilization site thereof.

In some embodiments, the skin-facing side of the pad has an adhesive thereon configured to adhere to skin of the patient.

In some embodiments, the catheter fasteners are spaced apart from each other to accommodate the extension port of the integrated catheter between the catheter fasteners when the integrated catheter is secured by the catheter fasteners on the platform.

In some embodiments, at least one catheter fastener of the pair of catheter fasteners is a 'C'-shaped clip connected to the catheter-securing side of the platform.

In some embodiments, at least one catheter fastener of the pair of catheter fasteners is a clamp having a first jaw connected to the catheter-securing side of the platform and a second jaw connected to the first jaw by a living hinge.

In some embodiments, the platform includes a plurality of through holes configured to enable moisture between the stabilization device and the patient to escape through the through holes when the stabilization device is adhered to the patient.

In some embodiments, the transverse axis of the platform is an axis of symmetry of the platform.

Also disclosed herein is a stabilization device for integrated catheters including, in some embodiments, a platform, a pair of catheter fasteners on the platform, and a pair of stabilization wings extending from the platform. The platform is a polymer-based platform having a skin-facing side and catheter-securing side of the platform. The pair of catheter fasteners is on the catheter-securing side of the platform. The catheter fasteners are configured to secure a hub of an integrated catheter having an extension port. The pair of stabilization wings extend from a transverse axis of the platform. The stabilization wings are configured to mitigate rotation of the integrated catheter about a longitudinal axis thereof when the integrated catheter is secured by the catheter fasteners on the platform and the stabilization device is adhered to a patient. The platform having twofold symmetry about the transverse axis of the platform.

In some embodiments, the platform is configured with a degree of flexibility enabling the platform to conform to a contour of the patient at a stabilization site thereof. The skin-facing side of the platform has an adhesive thereon configured to adhere to skin of the patient.

In some embodiments, the stabilization device further includes a pad of a foam-like material having a skin-facing side and a platform-facing side of the pad. The pad is configured with a degree of compressibility enabling the pad to conform to a contour of the patient at a stabilization site thereof. The skin-facing side of the pad has an adhesive thereon configured to adhere to skin of the patient.

In some embodiments, the catheter fasteners are spaced apart from each other to accommodate the extension port of the integrated catheter between the catheter fasteners when the integrated catheter is secured by the catheter fasteners on the platform.

In some embodiments, at least one catheter fastener of the pair of catheter fasteners is a 'C'-shaped clip connected to the catheter-securing side of the platform. The 'C'-shaped clip is configured with a degree of flexibility enabling an opening of the 'C'-shaped clip to initially expand when the hub of the integrated catheter is inserted into the opening and subsequently contract when the hub of the integrated catheter is inserted past the opening.

In some embodiments, at least one catheter fastener of the pair of catheter fasteners is a clamp having a first jaw connected to the catheter-securing side of the platform and a second jaw connected to the first jaw by a living hinge. The clamp is configured with a snap between the first jaw and the second jaw configured to snap the first and second jaws together after the hub of the integrated catheter is inserted into the clamp.

In some embodiments, the platform includes a plurality of through holes configured to enable moisture between the stabilization device and the patient to escape through the through holes when the stabilization device is adhered to the patient.

Also disclosed herein is a method for stabilizing integrated catheters including, in some embodiments, securing a hub of an integrated catheter in a pair of catheter fasteners on a catheter-securing side of a platform of a stabilization device, the catheter fasteners spaced apart from each other to accommodate an extension port of the integrated catheter between the catheter fasteners; removing an adhesive backing from a skin-facing side of the stabilization device to expose an adhesive; and adhering the stabilization device to skin at a stabilization site near a percutaneous insertion site of a patient, thereby stabilizing the integrated catheter and decreasing risk of mechanical phlebitis.

In some embodiments, securing the hub of the integrated catheter in the pair of catheter fasteners includes expanding an opening of at least one 'C'-shaped clip of the pair of catheter fasteners upon inserting the hub into the 'C'-shaped clip and allowing the opening of the 'C'-shaped clip to contract upon inserting the hub past the opening of the of the 'C'-shaped clip.

In some embodiments, securing the hub of the integrated catheter in the pair of catheter fasteners includes enclosing the hub within at least one clamp of the pair of catheter fasteners and snapping the clamp closed around the hub. The clamp has a first jaw connected to the catheter-securing side of the platform and a second jaw connected to the first jaw by a living hinge.

In some embodiments, the methods further includes degreasing the patient's skin at the stabilization site with a degreasing wipe before adhering the platform to the skin of the patient.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

With respect to terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Figure 1:
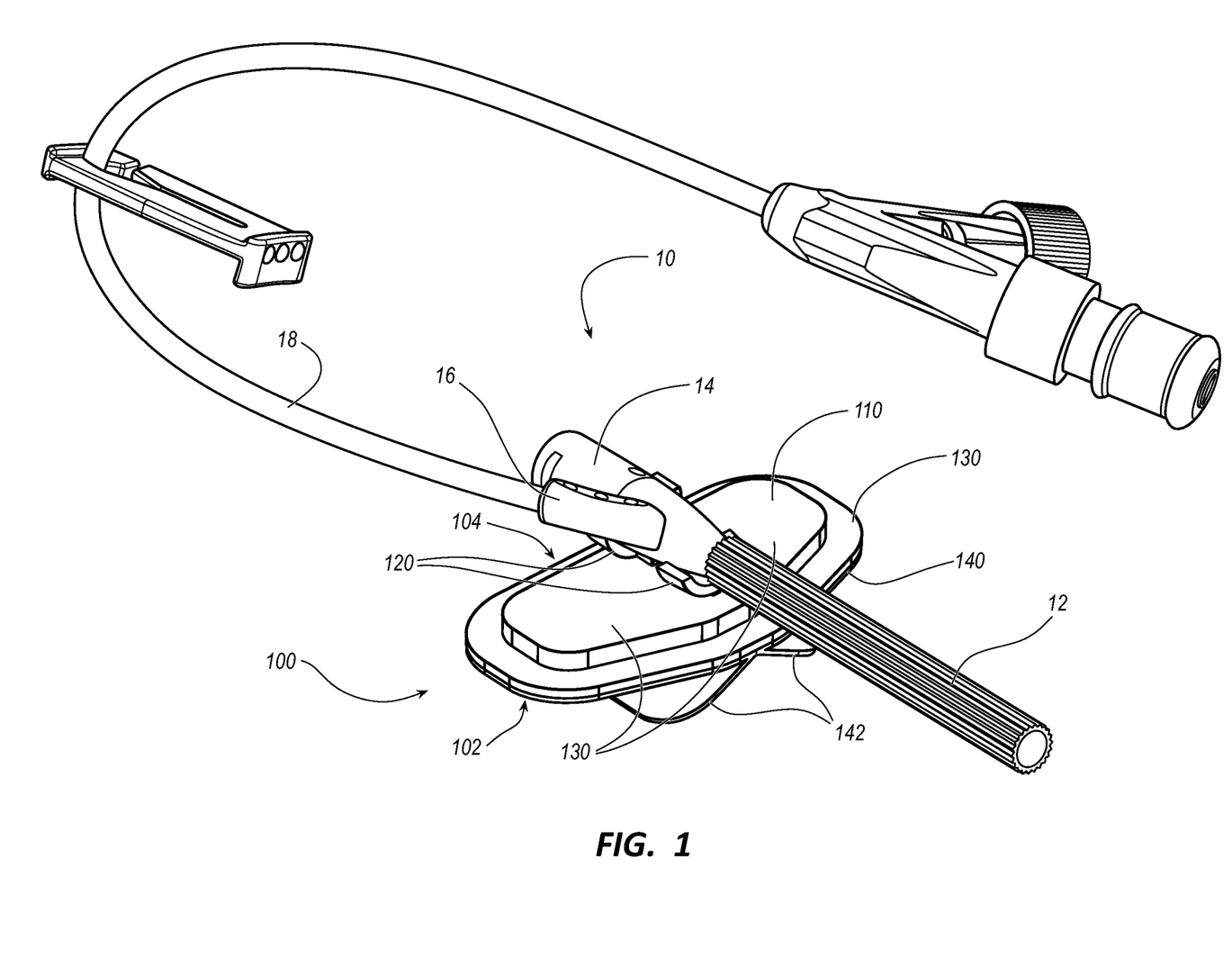
FIG. 1 illustrates a stabilization device for integrated catheters including an integrated catheter in accordance with some embodiments.

With respect to "integrated catheter," an integrated catheter is a one-piece manufacturer-assembled device including a catheter tube fluidly connected to at least one extension tube by way of a hub therebetween. Such an integrated catheter is shown in FIG. 1 by way of integrated catheter 10, which includes a catheter tube 12, a hub 14, an extension port 16 extending from the hub 14, and an extension tube 18 connected to the extension port 16. An integrated catheter is different than a non-integrated catheter, which must be assembled by a clinician or the like prior to use.

With respect to "proximal," as in a "proximal portion" or a "proximal end portion" of, for example, a catheter disclosed herein, "proximal" refers to a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," as in a "distal portion" or a "distal end portion" of, for example, a catheter disclosed herein, "distal" refers to a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Again, a PIVC often needs to be prematurely removed from a patient before an intended IV therapy is complete. A primary factor contributing to the need to prematurely remove a PIVC is mechanical phlebitis, which results when the PIVC moves and irritates the internal anatomy of the patient. A secondary factor contributing to the need to prematurely remove a PIVC is potential introduction of microorganisms when the PIVC moves while within the patient. Mechanical stabilization of PIVCs has been shown to decrease mechanical phlebitis and increase IV-therapy dwell time. However, existing stabilization devices for such PIVCs are not compatible with integrated PIVCs. Thus, the existing stabilization devices cannot provide the mechanical stabilization needed to reduce mechanical phlebitis and enhance the dwell time needed to complete intended IV therapies with integrated PIVCs. Disclosed herein is a stabilization device and methods thereof for integrated catheters such as integrated PIVCs.

For example, a stabilization device for integrated catheters is disclosed including, in some embodiments, a platform, a pair of catheter fasteners on the platform, and a pair of stabilization wings extending from the platform. The platform has a skin-facing side and catheter-securing side of the platform. The pair of catheter fasteners is on the catheter-securing side of the platform. The catheter fasteners are configured to secure a hub of an integrated catheter having an extension port. The pair of stabilization wings extend from a transverse axis of the platform. The stabilization wings are configured to mitigate rotation of the integrated catheter about a longitudinal axis thereof when the integrated catheter is secured by the catheter fasteners on the platform and the stabilization device is adhered to a patient. Also, a method for stabilizing integrated catheters with the stabilization device is disclosed.

Stabilization Device

FIG. 1 illustrates a stabilization device 100 for integrated catheters such as the integrated catheter 10 in accordance with some embodiments.

As shown in FIG. 1, some embodiments of the stabilization device 100 include a platform 110, a pair of catheter fasteners 120 on the platform 110, and a pair of stabilization wings 130 extending from the platform 110. The stabilization device 100, or the platform 110 thereof, has a skin-facing side 102 and catheter-securing side 104. The pair of catheter fasteners 120 is on the catheter-securing side 104 of the platform 110. The catheter fasteners 120 are configured to secure the hub 14 of the integrated catheter 10 with (or without) the extension port 16. As shown and described in more detail below with reference to FIGS. 4-6, the pair of stabilization wings 130 extend from a transverse axis 412 of the platform 110. The stabilization wings 130, which are shown as sweeping back from a distal end portion to a proximal end portion of the stabilization device 100, are configured to mitigate rotation of the integrated catheter 10 about a longitudinal axis thereof when both the integrated catheter 10 is secured by the catheter fasteners 120 on the platform 110 and the stabilization device 100 is adhered to a patient.

Also shown in FIG. 1, some embodiments of the stabilization device 100 also include a pad 130 adhered to the platform 110 and an adhesive backing 140 with optional wings 142 configured to facilitate removal of the adhesive backing from the pad 130 (or the platform 110, or the like, in some embodiments) for adhering the stabilization device 100 to a patient at a stabilization site thereof.

For expository expediency, "the stabilization device 100" of FIG. 1 is sometimes used herein to generically refer to some or all of the disclosed stabilization devices. In such instances, a certain component (e.g., "the platform 110") of the stabilization device 100 is sometimes used herein to generically refer to some or all of the disclosed stabilization-device components of the same kind. Because the stabilization device 100 and the components thereof can have unique features (e.g., the height $h_1$ of the platform 110 is greater than the height $h_2$ of the platform 510), context determines how "the stabilization device 100" and the components thereof are used.

Figure 2:
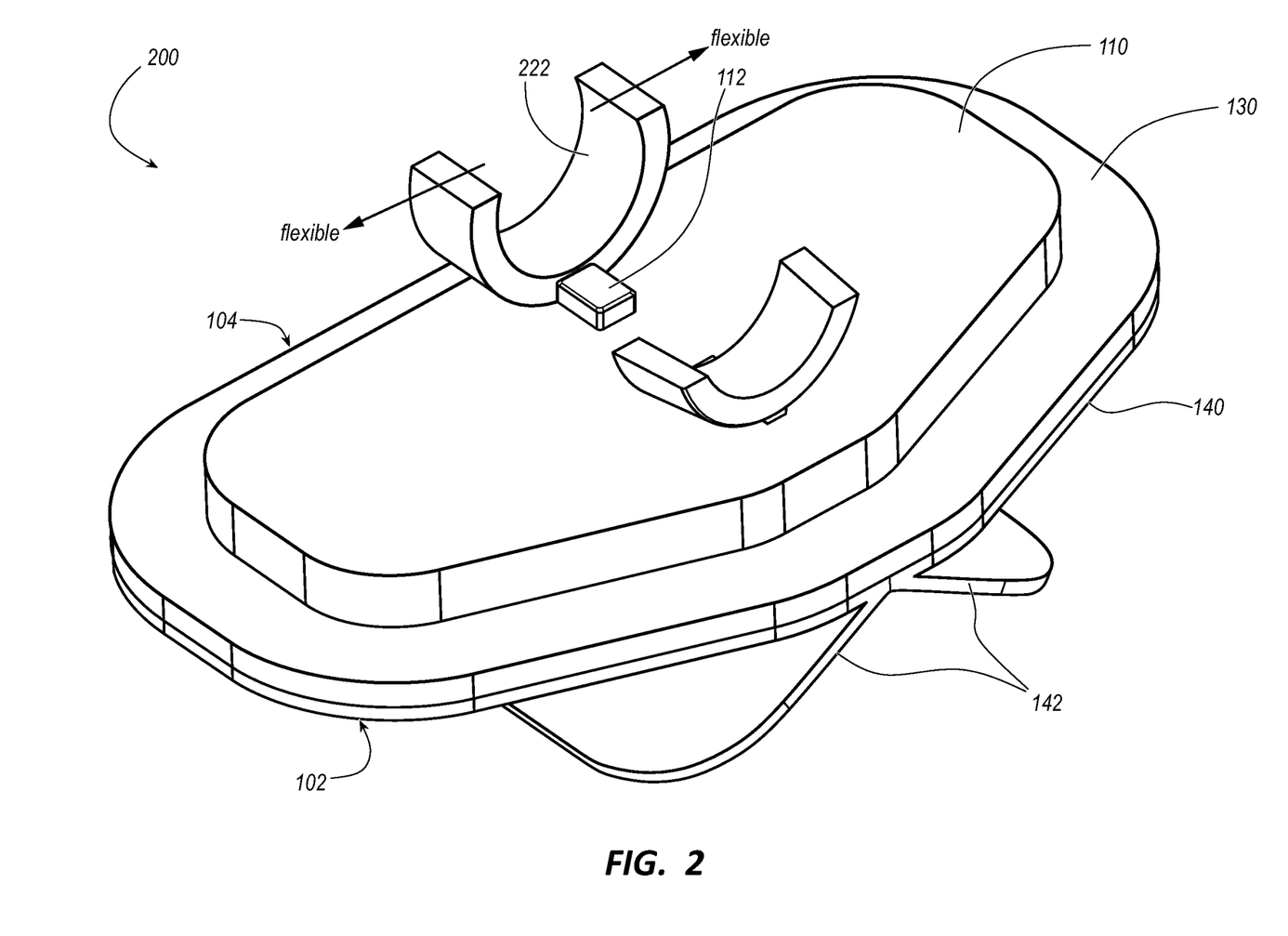
FIG. 2 illustrates a stabilization device including a 'C'-shaped clip for a catheter fastener in accordance with some embodiments.
Figure 3:
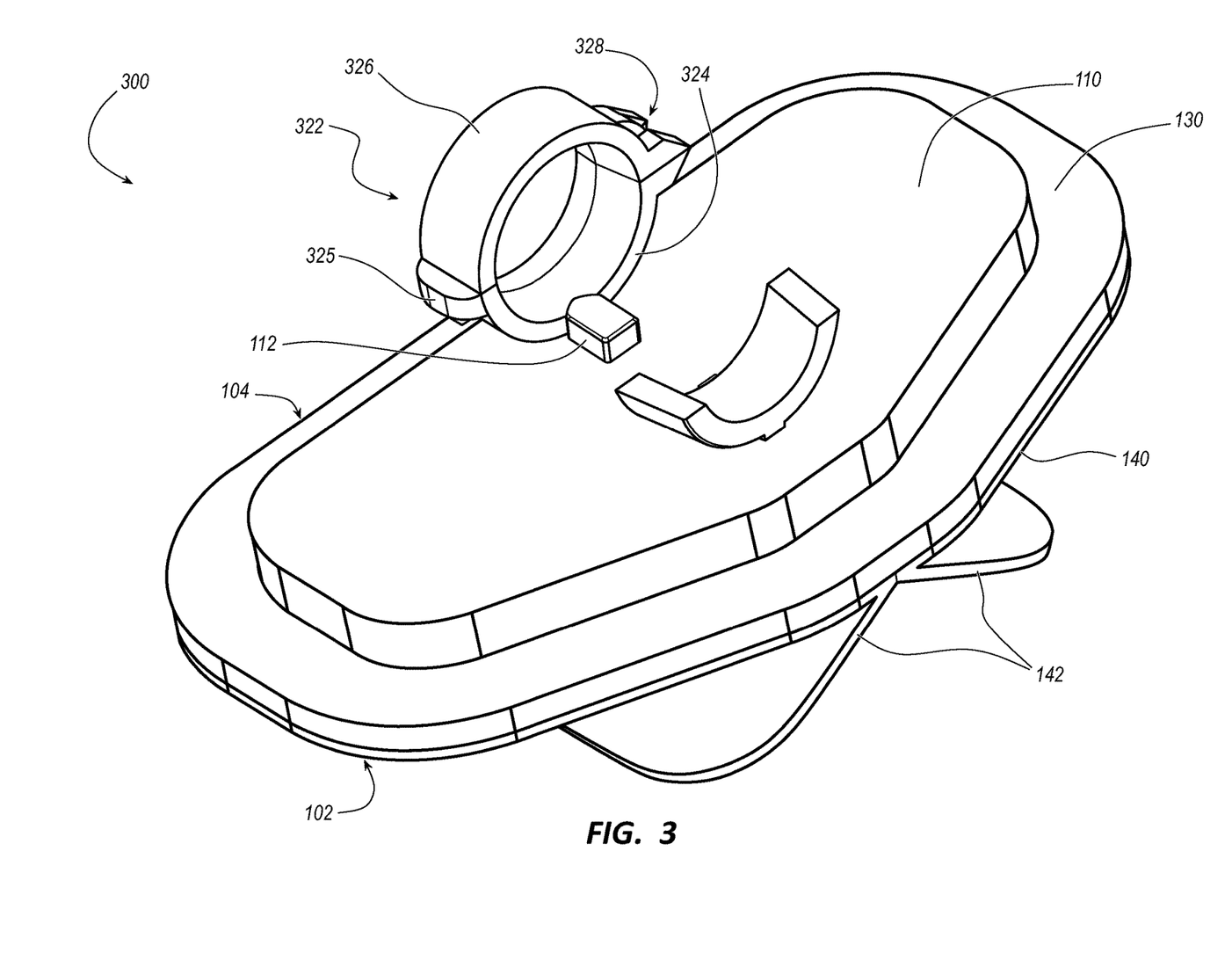
FIG. 3 illustrates a stabilization device including a clamp for a catheter fastener in accordance with some embodiments.

FIG. 2 illustrates a stabilization device 200 including at least one 'C'-shaped clip 222 for a catheter fastener of the catheter fasteners 120 in accordance with some embodiments. FIG. 3 illustrates a stabilization device 300 including at least one clamp 322 for a catheter fastener of the catheter fasteners 120 in accordance with some embodiments.

As shown in FIGS. 2 and 3, the catheter fasteners 120 in some embodiments of the stabilization device 100 such as the stabilization devices 200 and 300 are spaced apart from each other to accommodate the extension port 16 of the integrated catheter 10 between the catheter fasteners 120 when the integrated catheter 10 is secured by the catheter fasteners 120 on the platform 110. Between the catheter fasteners 120, the stabilization device 100 optionally includes a hub support 112 configured to support the hub 14 of the integrated catheter 10 between the catheter fasteners 120 when the integrated catheter 10 is secured by the catheter fasteners 120 on the platform 110.

As shown in FIG. 2, at least one catheter fastener of the pair of catheter fasteners 120 of the stabilization device 200 is the 'C'-shaped clip 222 connected to the catheter-securing side 104 of the platform 110. The 'C'-shaped clip 222 is configured with a degree of flexibility enabling an opening of the 'C'-shaped clip to initially expand when the hub 14 of the integrated catheter 10 is inserted into the opening. The 'C'-shaped clip 222 is configured to subsequently contract when the hub 14 of the integrated catheter 10 is inserted past the opening and seated in the 'C'-shaped clip 222.

As shown in FIG. 3, at least one catheter fastener of the pair of catheter fasteners 120 of the stabilization device 300 is the clamp 322 having a first jaw 324 connected to the catheter-securing side 104 of the platform 110 and a second jaw 326 connected to the first jaw 324 by a living hinge 325. The clamp 322 is configured with a snap 328 between the first jaw 324 and the second jaw 326 configured to snap the first jaw 324 and the second jaw 326 together when the hub 14 of the integrated catheter 10 is seated into the clamp 322.

Figure 4:
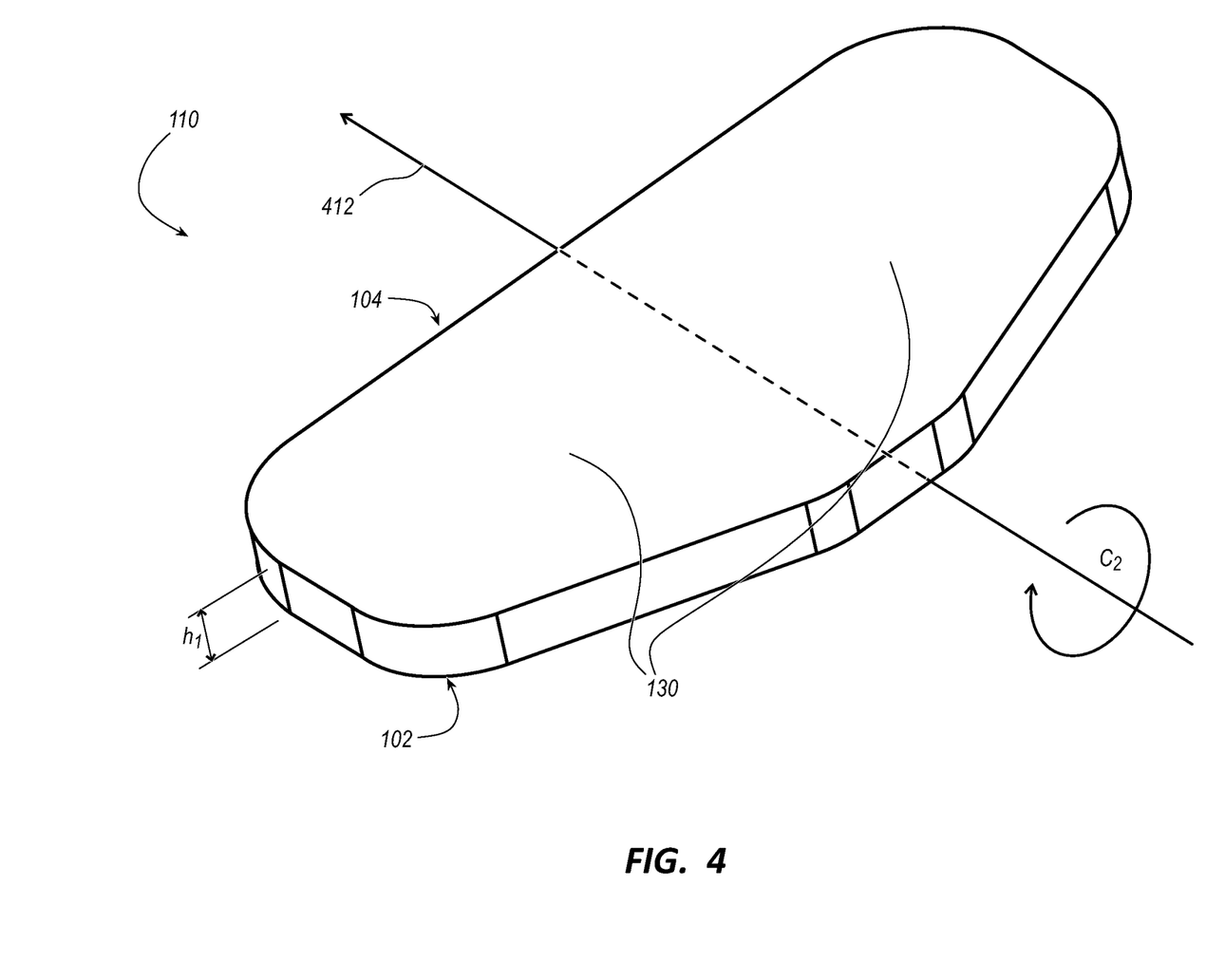
FIG. 4 illustrates a first platform for a stabilization device in accordance with some embodiments.
Figure 5:
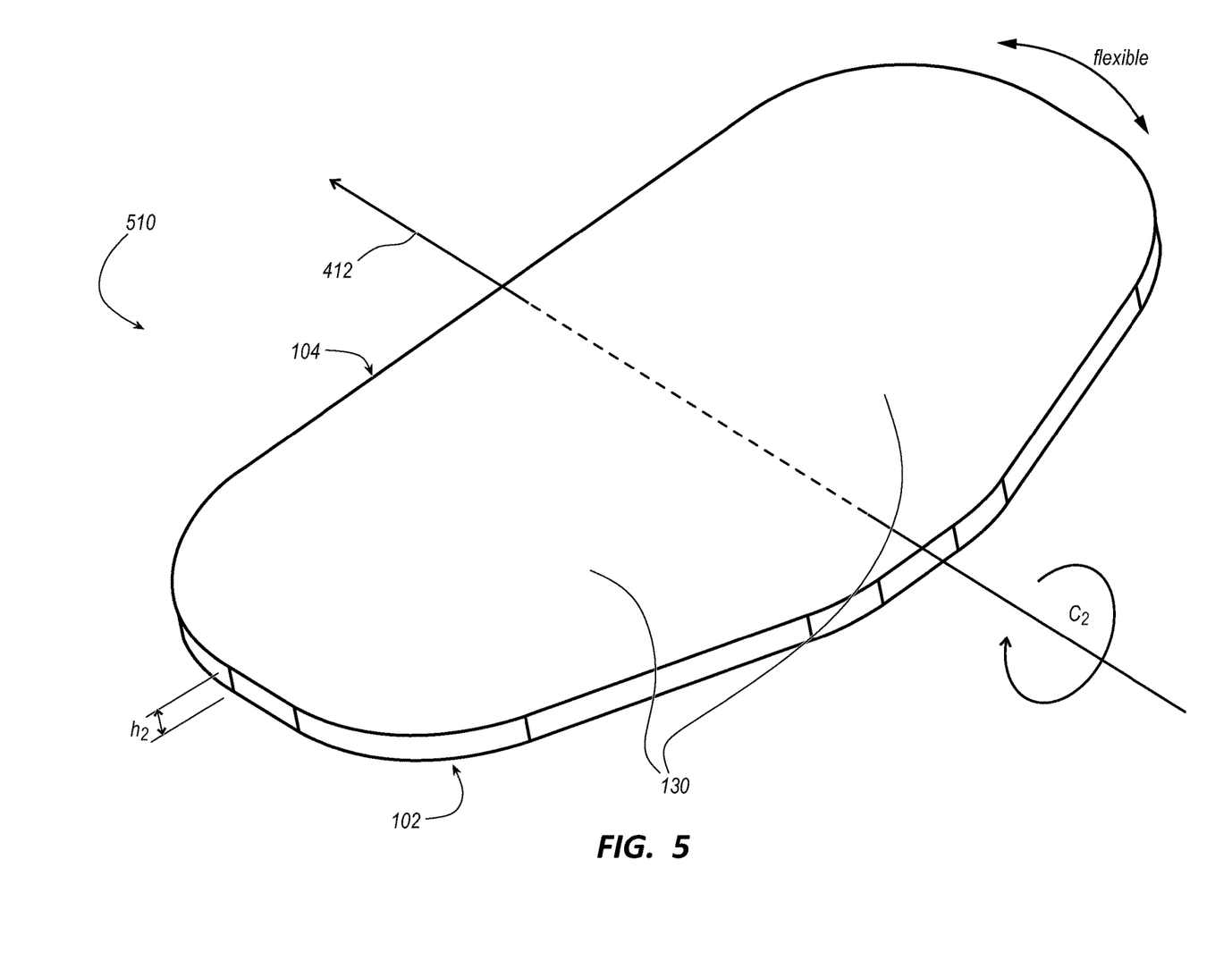
FIG. 5 illustrates a second platform for a stabilization device in accordance with some embodiments.
Figure 6:
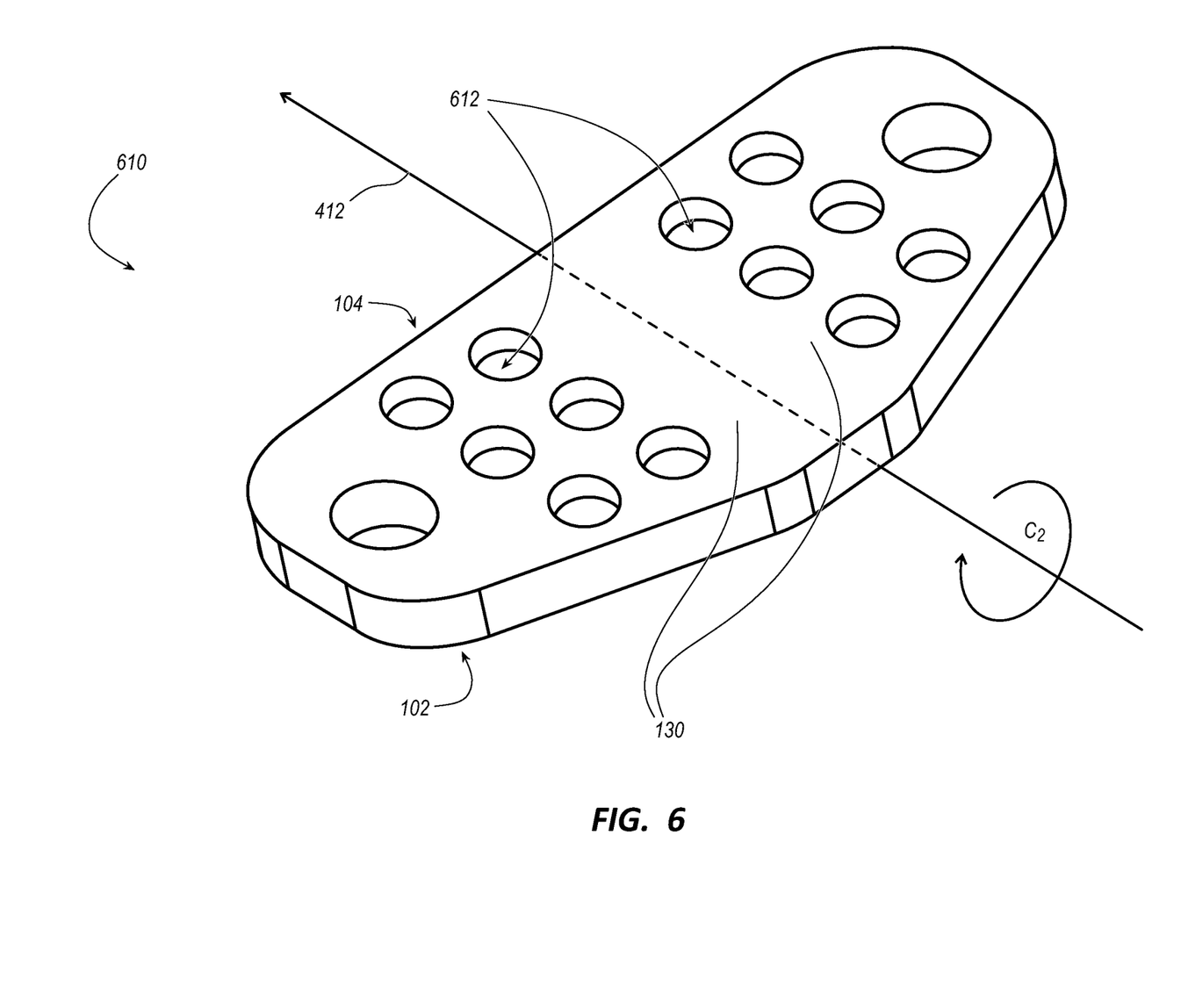
FIG. 6 illustrates a third platform for a stabilization device in accordance with some embodiments.
Figure 7:
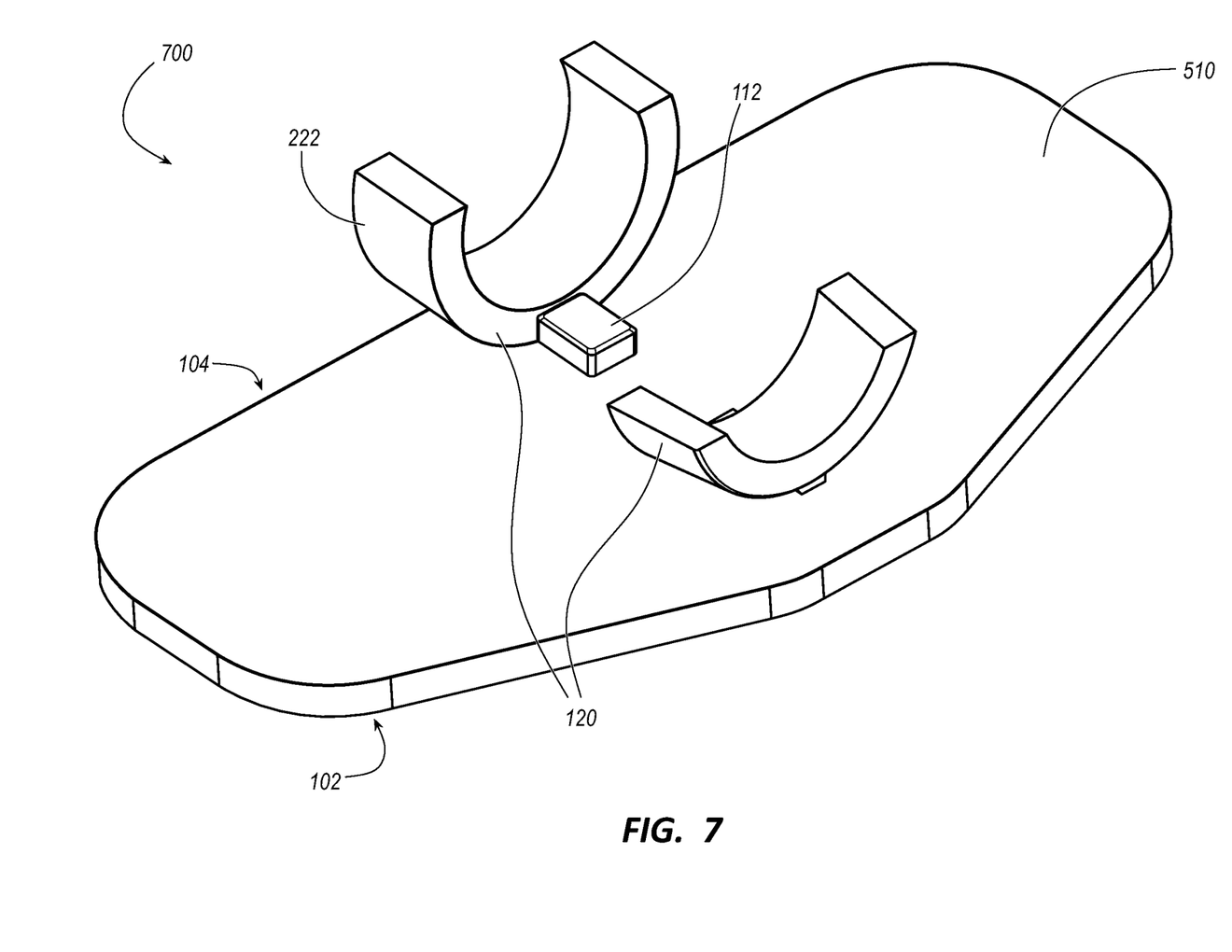
FIG. 7 illustrates a stabilization device including the platform of FIG. 5 in accordance with some embodiments.
Figure 8:
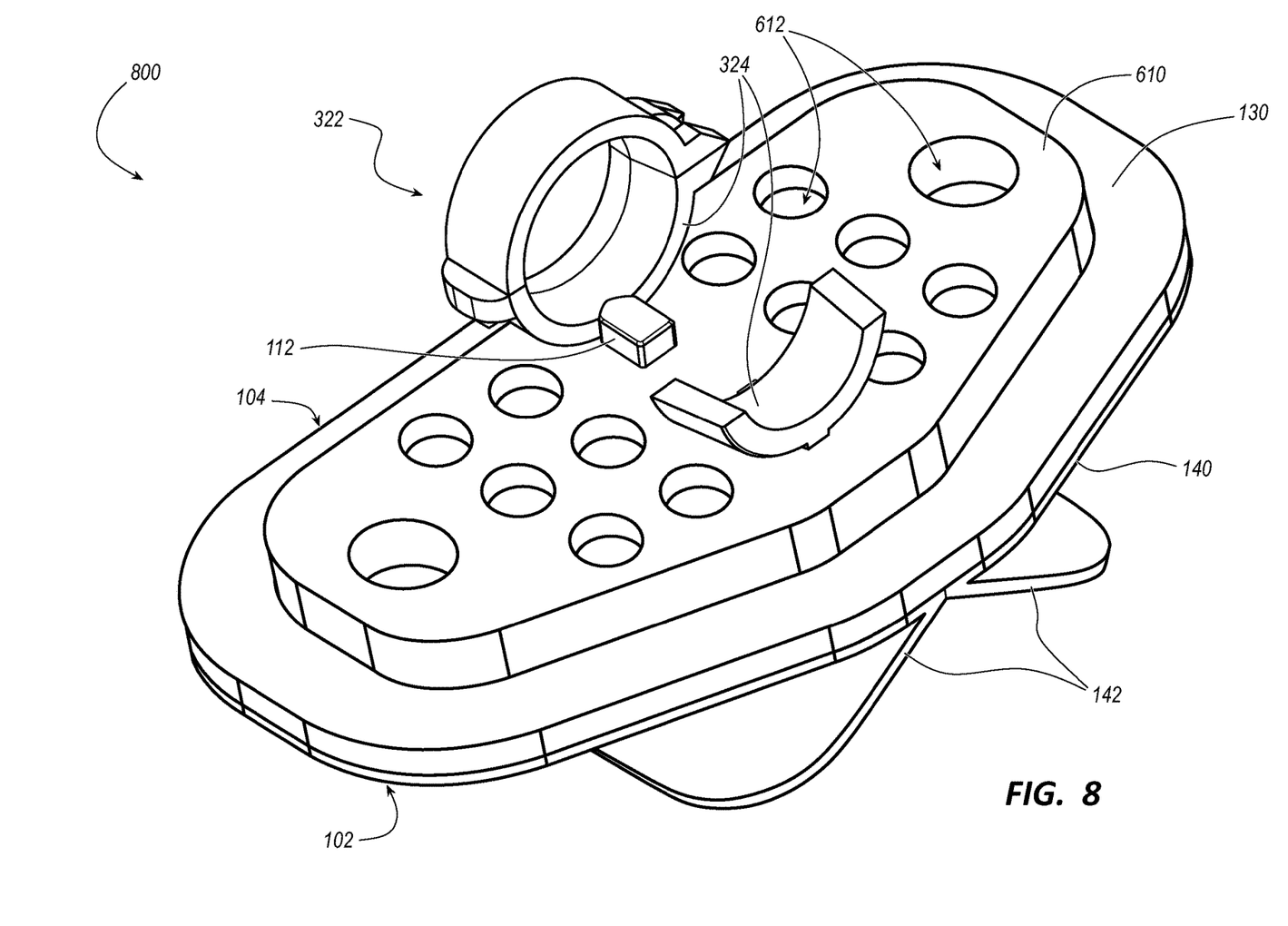
FIG. 8 illustrates a stabilization device including the platform of FIG. 6 in accordance with some embodiments.

FIG. 4 illustrates a first platform (i.e., the platform 110) for the stabilization device 100 in accordance with some embodiments. FIG. 5 illustrates a second platform 510 for the stabilization device 100 in accordance with some embodiments. FIG. 6 illustrates a third platform 610 for the stabilization device 100 in accordance with some embodiments. FIG. 7 illustrates a stabilization device 700 including the platform 510 of FIG. 5 in accordance with some embodiments. FIG. 8 illustrates a stabilization device 800 including the platform 610 of FIG. 6 in accordance with some embodiments.

As shown in FIGS. 4, 5, and 6, each platform of the platforms 110, 510, and 610 includes the transverse axis 412 from which the pair of stabilization wings 130 extend. The transverse axis 412 is an axis of symmetry about which the platform 110, 510, or 610 has twofold rotational symmetry (i.e., $C_2$ symmetry).

As shown in FIG. 5, the platform 510 has a height $h_2$ that is less than a height $h_1$ of the platform 110. Being as the platform 510 is relatively thin and formed of a medically acceptable polymer as described below, the platform 510 is configured with a degree of flexibility enabling the platform 510 to conform to a contour (e.g., a body contour) of a patient at a stabilization site thereof near a percutaneous insertion site for the integrated catheter 10. In contrast, while the platform 110 can be formed of the same polymer as the platform 510, the platform 110 has little to no appreciable flexibility due to the height $h_1$ of the platform 110 being greater than the height $h_2$ of the platform 510. For this reason, the platform 110 is often used with the pad 130, which has a degree of compressibility as described herein. In some embodiments, the platform 510 is also used with the pad 130, thereby increasing conformation of the stabilization device 100 to the contour (e.g., the body contour) of the patient.

The skin-facing side 104 of the platform 510 includes an adhesive (e.g., pressure-sensitive adhesive) thereon configured to adhere to the skin of the patient as with the stabilization device 700 of FIG. 7, from which the adhesive backing 140 is removed for clarity. Alternatively, like the platform 110, the skin-facing side 104 of the platform 510 is adhered to the pad 130, which pad 130, in turn, includes an adhesive (e.g., pressure-sensitive adhesive) on the skin-facing side 104 of the pad 130 configured to adhere to the skin of the patient upon removal of the adhesive backing 140. The adhesive between the pad 130 and the platform 510 that adheres the pad 130 and the platform 510 together can be the same or different then than the adhesive that adheres the stabilization device to the patient.

With respect to the pad 130, the pad 130 of the stabilization device 100 is formed of a medically acceptable foam-like material having a degree of compressibility also enabling the pad 130 to conform to a contour (e.g., a body contour) of a patient at a stabilization site thereof near a percutaneous insertion site for the integrated catheter 10. Again, the skin-facing side 104 of the pad 130 includes an adhesive (e.g., pressure-sensitive adhesive) thereon configured to adhere to the skin of the patient. (See, for example, the stabilization device 200 of FIG. 2, the stabilization device 300 of FIG. 3, or the stabilization device 800 of FIG. 8.)

As shown in FIG. 6, the platform 610 includes a plurality of through holes 612, or breathing holes, configured to enable moisture between, for example, the stabilization device 800 of FIG. 8 and the skin of the patient to escape through the through holes 612 when the stabilization device 800 is adhered to the patient. While not shown, the platform 510 can also include the plurality of through holes 612.

The platform 110, 510, or 610 is formed of a polymeric material such as by injection molding. For example, the platform 510, which is relatively thin and flexible compared to the platform 110, can be formed by injection molding including thin-wall molding. The pair of catheter fasteners 120 can be molded together with the platform 110, 510, or 610 or coupled to the platform 110, 510, or 610 after each of the pair of fasteners 120 and the platform 110, 510, or 610 is molded.

In view of the foregoing description, it should be understood any platform 110, 510, or 610, or a combination thereof, disposed on the pad 130 or not, can include any pair of catheter fasteners 120 described herein to form a stabilization device such as the stabilization device 200, 300, 700, or 800.

Kit

The stabilization device 100, instructions for use of the stabilization device 100, and any one or more additional components selected from the integrated catheter 10, an antimicrobial pad (e.g., BIOPATCH®, GuardIVa®), a topical medicament optionally including an antimicrobial agent, a skin adhesive optionally including an antimicrobial agent, and a degreasing wipe can be packaged as a ready-to-use stabilization kit.

Method

A method for stabilizing integrated catheters such as the integrated catheter 10 includes, in some embodiments, securing the hub 14 of the integrated catheter 10 in the pair of catheter fasteners 120 on the catheter-securing side 104 of the platform 110 of the stabilization device 100, the catheter fasteners 120 spaced apart from each other to accommodate the extension port 16 of the integrated catheter 10 between the catheter fasteners 120; removing an adhesive backing 140 from the skin-facing side 102 of the stabilization device 100 to expose the adhesive; and adhering the stabilization device 100 to skin of the patient at a stabilization site thereof near a percutaneous insertion site, thereby stabilizing the integrated catheter 10 and decreasing risk of mechanical phlebitis.

Securing the hub 14 of the integrated catheter 10 in the pair of catheter fasteners 120 includes expanding the opening of the 'C'-shaped clip 222 of the pair of catheter fasteners 120 upon inserting the hub 14 into the 'C'-shaped clip 222 and allowing the opening of the 'C'-shaped clip 222 to contract upon inserting the hub 14 past the opening of the of the 'C'-shaped clip 222. Alternatively, securing the hub 14 of the integrated catheter 10 in the pair of catheter fasteners 120 includes enclosing the hub 14 within the clamp 322 of the pair of catheter fasteners 120 and snapping the clamp 322 closed around the hub 14.

The method can further include accessing the percutaneous insertion site in one or more ways of accessing the insertion site such as passing the catheter tube 12 of the integrated catheter 10 into the insertion site.

The method can further include treating the percutaneous insertion site after accessing the insertion site. Treating the insertion site can include placing the antimicrobial pad (e.g., BIOPATCH®, GuardIVa®) around the insertion site to keep the insertion site free of infection. Treating the insertion site can include applying the topical medicament optionally including the antimicrobial agent around the insertion site or sealing the insertion site with the skin adhesive optionally including a same or different antimicrobial agent. Not only does sealing the insertion site with the skin adhesive prevent microbes from entering the insertion site, but sealing the insertion site has the added effect of further stabilizing the integrated catheter 10 to the patient, thereby further decreasing mechanical phlebitis.

The method can further include degreasing the skin of the patient at the stabilization site with a degreasing wipe before adhering the stabilization device 100 to the skin of the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter kit, comprising:
   an integrated catheter comprising a hub; and
   a stabilization device, comprising:
      a platform;
      first and second stabilization wings extending from a transverse axis of the platform under the platform, the first and second stabilization wings configured to mitigate rotation of the integrated catheter about a longitudinal axis of the integrated catheter when the integrated catheter is secured to the platform;
      a first catheter fastener positioned on the platform; and
      a second catheter fastener positioned on the platform disconnected from the first catheter fastener, the first catheter fastener and the second catheter fastener configured to secure the hub of the integrated catheter.

2. The catheter kit according to claim 1, wherein the hub of the integrated catheter includes an extension port coupled to an extension tube.

3. The catheter kit according to claim 2, wherein the first catheter fastener is separated from the second catheter fastener a sufficient distance to accommodate the extension port of the hub of the integrated catheter.

4. The catheter kit according to claim 1, wherein the platform is configured with a degree of flexibility enabling the platform to conform to a contour of a patient at a stabilization site.

5. The catheter kit according to claim 1, wherein the platform includes an adhesive configured to adhere to skin of a patient.

6. The catheter kit according to claim 1, wherein the stabilization device further comprises a pad formed of a compressible material to enable the pad to conform to a contour of a patient at a stabilization site.

7. The catheter kit according to claim 6, wherein the pad comprises an adhesive configured to adhere to skin of the patient.

8. The catheter kit according to claim 1, wherein the first catheter fastener is a 'C'-shaped clip connected to the platform.

9. The catheter kit according to claim 8, wherein the 'C'-shaped clip is configured with a degree of flexibility enabling an opening of the 'C'-shaped clip to initially expand when the hub of the integrated catheter is inserted into the opening and to subsequently contract when the hub of the integrated catheter is inserted past the opening.

10. The catheter kit according to claim 1, wherein at least one of the first catheter fastener and the second catheter fastener is a clamp having a first jaw connected to the platform and a second jaw connected to the first jaw by a living hinge.

11. The catheter kit according to claim 10, wherein the clamp is configured with a snap between the first jaw and the second jaw configured to snap the first jaw and the second jaw together after the hub of the integrated catheter is inserted into the clamp.

12. The catheter kit according to claim 1, wherein the transverse axis of the platform is an axis of symmetry of the platform.

13. The catheter kit according to claim 1, wherein the platform has twofold symmetry about the transverse axis of the platform.

14. The catheter kit according to claim 1, wherein the platform is formed of a polymer material.

15. The catheter kit according to claim 1, wherein the platform includes a plurality of through holes configured to enable moisture to escape through the plurality of through holes when the stabilization device is adhered to a patient.

* * * * *